US00PP11962P2

(12) United States Plant Patent
Gold

(10) Patent No.: US PP11,962 P2
(45) Date of Patent: Jun. 26, 2001

(54) MARANTA PLANT NAMED 'BEAUTY KIM'

(75) Inventor: Brian Gold, Centerville, UT (US)

(73) Assignee: Oro Farms, Centerville, UT (US)

( * ) Notice: Subject to any disclaimer, the term of this patent is extended or adjusted under 35 U.S.C. 154(b) by 0 days.

(21) Appl. No.: 09/475,971

(22) Filed: Dec. 31, 1999

(51) Int. Cl.[7] ..... A01H 5/00

(52) U.S. Cl. ..... Plt./373

(58) Field of Search ..... Plt./263, 373

*Primary Examiner*—Bruce R. Campell
*Assistant Examiner*—June Hwu
(74) *Attorney, Agent, or Firm*—C. A. Whealy

(57) ABSTRACT

A distinct cultivar of Maranta plant named Beauty Kim, characterized by its outwardly spreading to weeping plant habit and unique leaf coloration.

1 Drawing Sheet

BACKGROUND OF THE INVENTION

The present invention relates to a new and distinct cultivar of Maranta plant, botanically known as *Maranta leuconeura*, and hereinafter referred to by the cultivar name Beauty Kim.

The new Maranta was discovered by the Inventor in a controlled environment in San Jose Penula, Guatemala, in Spring, 1997, as a naturally-occurring whole plant mutation of the *Maranta leuconeura* var. Kerchoviana, not patented. The new Maranta was observed as a single plant in a group of plants of the var. Kerchoviana.

Asexual propagation of the new Maranta by vegetative cuttings and by tissue-culture in Apopka, Fla. has shown that the unique features of this new Maranta are stable and reproduced true to type in successive generations.

The new Maranta has not been observed under all possible environmental conditions. The phenotype may vary somewhat with variations in environment such as temperature and light intensity, without, however, any variance in genotype.

SUMMARY OF THE INVENTION

The following traits have been repeatedly observed and are determined to be in unique characteristics of plants of the new Maranta. These characteristics in combination distinguish the new Maranta as a new and distinct cultivar:

1. Outwardly spreading to weeping plant habit.
2. Unique leaf coloration.

Plants of the new Maranta differ from the var. Kerchoviana and other known selections and cultivars of Maranta in leaf coloration and pattern. The upper surface foliage colors of the new Maranta, the parent var. Kerchoviana and the var. Massangeana compare as follows:

| | Background | Spots | Veins | Venal splotches |
|---|---|---|---|---|
| 'Beauty Kim' | 139C | 175D and 183A | 150D and 139C | 150D |
| var. Kerchoviana | 137A | 139A | 137A | none |
| var. Massangeana | 137B | 144C | 53B | none |

BRIEF DESCRIPTION OF THE PHOTOGRAPHS

The accompanying colored photographs illustrate the overall appearance of the new Maranta, showing the colors as true as it is reasonably possible to obtain in colored reproductions of this type. Colors in the photographs may differ slightly from the color values cited in the detailed botanical description which more accurately describe the actual colors of the new Maranta. The photograph at the top of the sheet comprises a side perspective view of a typical potted plant of the new Maranta. The photograph at the bottom of the sheet comprises a close-up view of typical leaves of the new Maranta, the parent var. Kerchoviana and the var. Massangeana (left to right).

DETAILED BOTANICAL DESCRIPTION

The new Maranta has not been observed under all possible environmental conditions. The phenotype may vary somewhat with variations in environment such as temperature and light intensity, without, however, any variance in genotype.

The following measurements and observations were taken from plants grown in Apopka, Fla., in a double-layered polyethylene-covered greenhouse with day temperatures about 21 to 32° C., night temperatures about 18 to 21° C., and light levels about 1,500 to 2,000 foot-candles. Plants measured were about 12 weeks from planting a rooted tissue-cultured plant into a 10-cm container.

In the following description, color references are made to The Royal Horticultural Society Colour Chart except where general terms of ordinary dictionary significance are used.

Botanical classification: *Maranta leuconeura* cultivar Beauty Kim.

Parentage: Naturally-occurring whole plant mutation of *Maranta leuconeura* var. Kerchoviana, not patented.

Propagation:

*Type.*—By vegetative cuttings.

*Time to initiate roots.*—About 3 weeks at 21° C.

*Time to produce a rooted cutting.*—About 5 weeks at 21° C.

*Root description.*—Numerous, freely branching.

Plant description:

*Plant shape.*—Rounded, mounded, low-growing, and outwardly spreading to weeping.

*Growth habit.*—Bushy, dense and full.

*Crop time.*—From a rooted cutting or tissue-cultured liner, about 12 weeks are required to produce a finished 10-cm container. Appropriate for 10-cm and larger containers.

*Plant height.*—About 10 cm from soil level to top of leaf plane.

*Plant diameter.*—About 15 cm.

*Plant vigor.*—Moderately vigorous.

*Branching habit.*—Moderately basal-branching. Pinching is typically not required.

*Stems.*—Length: About 5 cm. Diameter: About 5 mm. Internode length: About 2.5 cm. Color: 200A.

*Foliage description.*—Arrangement: Alternate. Length: About 12 cm. Diameter: About 8.5 cm. Shape: Oval; oblong-elliptic. Apex: Rounded; cuspidate. Base: Rounded; obtuse. Margin: Entire. Texture: Smooth; leathery. Color: Young leaves, upper surface: Background, 139C; spots, 175D and 183A; veins, 150D and 139C; random venal splotches, 150D. Young leaves, lower surface: 138B. Mature leaves, upper surface: Background, 139C; spots, 175D and 183A; veins, 150D and 139C; random venal splotches. 150D. Mature leaves, lower surface: 138B. Petiole: Length: About 5 cm. Diameter: About 2.5 mm. Color: 200A.

Flower description: Flowers have not been observed on plants of the new Maranta.

Low temperature tolerance: Plants of the new Maranta are tropical and do not tolerate freezing temperatures.

Disease resistance: Resistance to known pathogens common to Maranta has not been observed on plants grown under commercial production conditions.

It is claimed:

1. A new and distinct cultivar of Maranta plant named Beauty Kim, as illustrated and described.

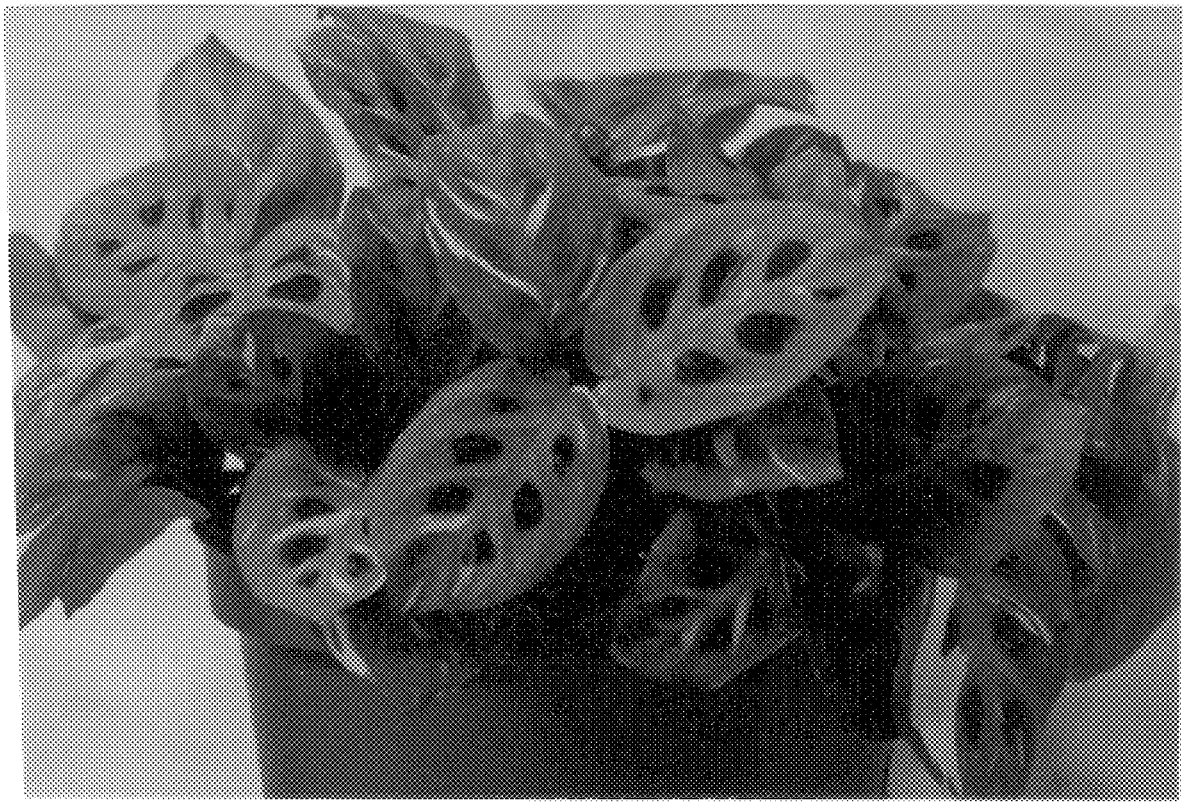
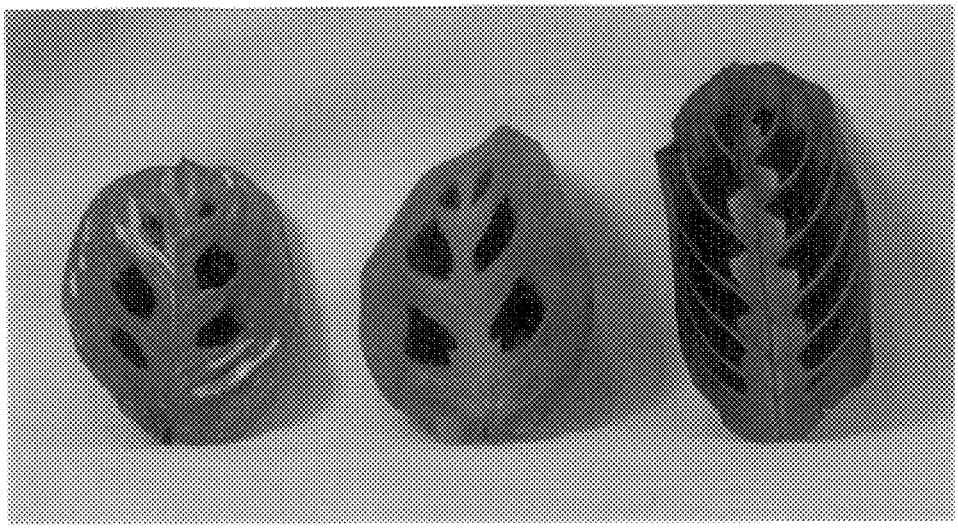

* * * * *